(12) United States Patent
Weissbach Otte

(10) Patent No.: US 7,771,196 B2
(45) Date of Patent: Aug. 10, 2010

(54) ORTHODONTIC APPLIANCE

(76) Inventor: Klaus Weissbach Otte, Koernickestrasse 10, 55543 Bad Kreuznach (DE)

( * ) Notice: Subject to any disclaimer, the term of this patent is extended or adjusted under 35 U.S.C. 154(b) by 145 days.

(21) Appl. No.: 11/730,579

(22) Filed: Apr. 2, 2007

(65) Prior Publication Data

US 2008/0220388 A1     Sep. 11, 2008

(30) Foreign Application Priority Data

Apr. 1, 2006    (DE) .................. 10 2006 015 290

(51) Int. Cl.
*A61C 7/10*  (2006.01)
(52) U.S. Cl. ............................................. 433/7
(58) Field of Classification Search .............. 433/6, 433/7, 18, 19, 20, 21, 24
See application file for complete search history.

(56) References Cited

U.S. PATENT DOCUMENTS

| | | | | |
|---|---|---|---|---|
| 4,347,054 A | * | 8/1982 | Kraus et al. | ............ 433/7 |
| 4,379,693 A | | 4/1983 | Wallshein | |
| 5,439,377 A | * | 8/1995 | Milanovich | ............ 433/7 |
| 5,785,520 A | | 7/1998 | Carano | |
| 5,885,290 A | * | 3/1999 | Guerrero et al. | ............ 606/71 |
| 6,435,870 B1 | * | 8/2002 | Walde | ............ 433/7 |
| 6,655,959 B2 | * | 12/2003 | Farzin-Nia et al. | ............ 433/18 |
| 2003/0091952 A1 | * | 5/2003 | Bowman et al. | ............ 433/18 |

FOREIGN PATENT DOCUMENTS

| | | |
|---|---|---|
| DE | 1566260 | 8/1970 |
| DE | 29613253 | 10/1996 |
| DE | 19953824 | 5/2000 |
| DE | 10053706 | 5/2002 |
| WO | WO 02/26155 A2 | 4/2002 |
| WO | 2004/103200 | 12/2004 |

OTHER PUBLICATIONS

European Search Report dated Jul. 5, 2007 from counterpart European patent application.

* cited by examiner

*Primary Examiner*—Cris L Rodriguez
*Assistant Examiner*—Michael R Ballinger
(74) *Attorney, Agent, or Firm*—Timothy J. Klima; Shuttleworth & Ingersoll, PLC

(57) ABSTRACT

An orthodontic appliance for distalizing opposed molars (2, 3) of the upper jaw of a patient, in which the device (4) has a bracing plate (5), which in its intended use rests on the palate of the patient, and which can be secured, via wire elements (6-9) disposed on the bracing plate (5), to opposed teeth (10-13) that are located anteriorly of the molars (2, 3) to be distalized. The appliance (4), with which the molars (2, 3) to be distalized can be moved individually backward as needed, includes a one-piece bracing plate (5), on the posterior end (14) of which two force modules (15, 16), spaced laterally apart from one another and adjustable independently of one another, are connected to the bracing plate, each being connectable via a respective elastic spring arm (17, 18) to one of the molars (2, 3) to be distalized.

4 Claims, 2 Drawing Sheets

ORTHODONTIC APPLIANCE

Figure 1:
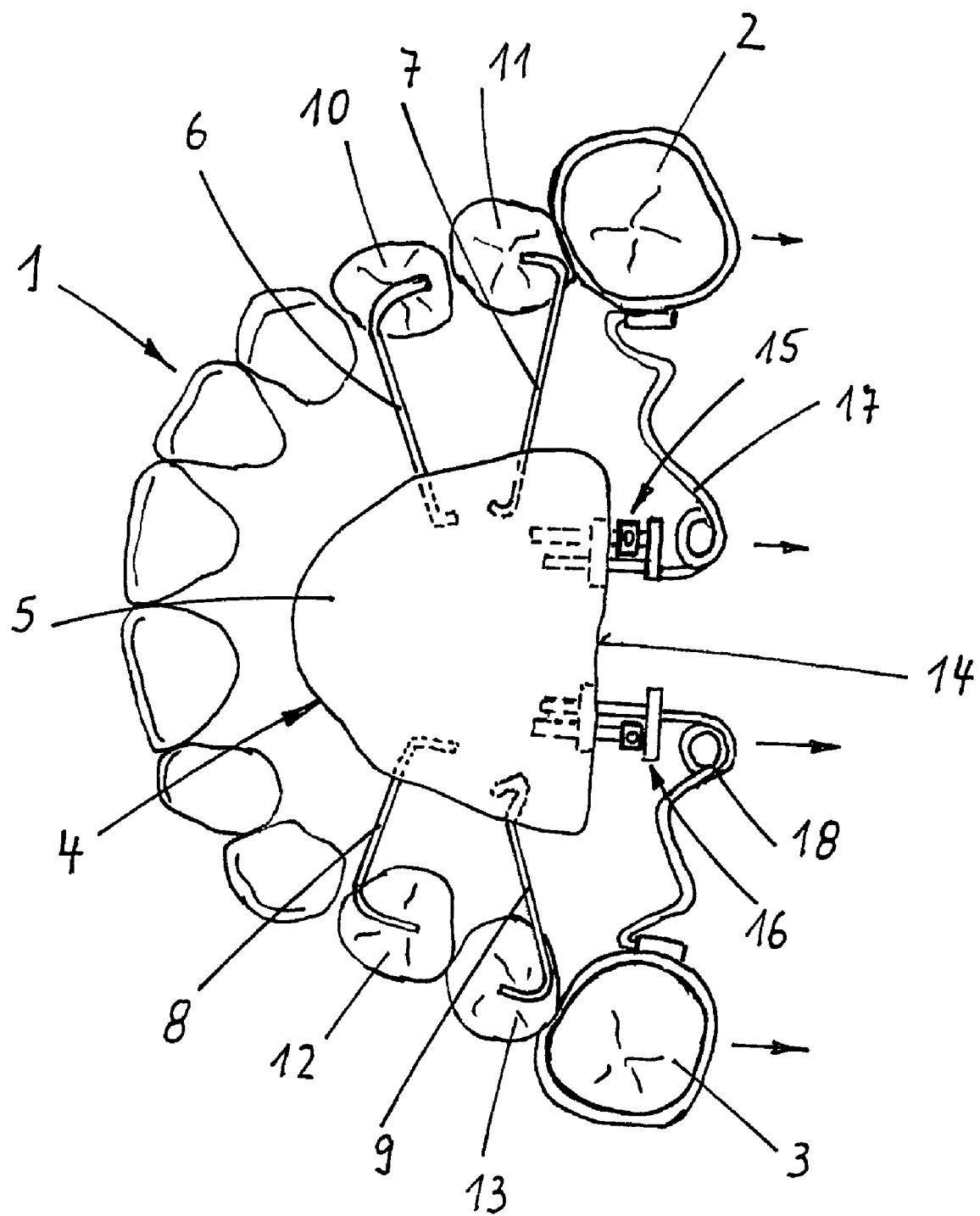

This application claims priority to German Patent Application DE10 2006 015 290.5 filed Apr. 1, 2006, the entirety of which is incorporated by reference herein.

The invention relates to an orthodontic appliance for distalizing opposed molars of the upper jaw.

For dental regulation of the molars, it is known to use an orthodontic appliance which is also known as a distalizing apparatus or pendulum apparatus. As a rule, what takes place is a reverse motion (distalizing) of the molars (cheek teeth) in the upper jaw.

The known devices each have a bracing plate (known as a Nance plate) of plastic that rests on the patient's palate and that is releasably secured to opposed teeth (as a rule, the bicuspids) via wire elements disposed laterally on the bracing plate. To accomplish the desired distalizing of the two molars in the upper jaw, a rear portion of the bracing plate is joined displaceably, via a force or activation module, to the remaining region of the bracing plate. The rear region in turn acts on the two molars to be distalized via two elastic spring arms that are spaced apart from one another.

The force module disposed between the parts of the bracing plate is essentially a threaded rod, which with its contrary thread can be screwed into and out of both parts of the bracing plate, so that depending on the direction of rotation of the threaded rod, the two parts of the bracing plate move either away from one another or toward one another. To avoid relative rotation of the two parts of the bracing plate upon actuation of the threaded rod, guide rods are provided to the right and left of the threaded rod.

One disadvantage, among others, of the known orthodontic appliances is that upon an actuation of the threaded rod, a simultaneous motion of the left and right molars occurs. This can cause even correctly positioned teeth that may be located on one of the two sides to be shifted and thus disadvantageously changed in their position.

The object of the invention is to disclose a simply constructed and geometrically small orthodontic appliance for distalizing the molars of the upper jaw, with which the right and left molars to be distalized, as needed, can be moved individually backward.

This object is attained according to the invention by the characteristics of claim 1. Further, especially advantageous features of the invention are disclosed in the dependent claims.

The invention is based essentially on the concept of using a one-piece bracing plate, instead of a two-piece bracing plate, and of providing two force modules on the posterior end of this bracing plate, which are spaced laterally apart from one another and are adjustable independently of one another and which can each be connected via an elastic spring arm to one of the two molars to be distalized.

By means of this kind of disposition of two separate force modules, it is easily possible to perform an orthodontic treatment targeted to the particular degree of mispositioning of the individual tooth.

In a first advantageous embodiment of the invention, the applicable force element of the device of the invention has a threaded rod that can be screwed into and out of the bracing plate and also has a connecting part that is axially displaceable with the threaded rod but is secure from rotation. The connecting part extends perpendicular to the longitudinal axis of the threaded rod, and a rodlike guide element extending parallel to the threaded rod is secured to the connecting part and on the one hand displaceabiy engages a guide recess in the bracing plate and on the other is joined to the end region of the elastic spring arm associated with the force module.

The rodlike guide element may comprise a type of alloy known in dentistry, such as high-grade steel, while the elastic spring arm should preferably comprise a titanium-molybdenum alloy, since that material has especially advantageous elastic properties.

In the production of the mechanical connection between the guide element, comprising the aforementioned alloy type, that is, high-grade steel, and the spring arm comprising a titanium-molybdenum alloy, the various properties of the two materials should be taken into account. For instance, titanium-molybdenum alloys upon relatively strong heating, as occurs in hard soldering, lose their elasticity and thus their orthodontic effectiveness because of microscopic structural changes. Moreover, the solder, which already melts at low temperatures, may often not be biocompatible and/or may contain toxic substances.

It has therefore proved advantageous not to join the applicable guide element to the corresponding spring arm by hard soldering but instead alternatively to do so by means of an adhesive bond or a press fit or clamping fit.

To make it possible to perform such a connection in a simple way, the rodlike guide element may for instance be embodied as a tube, into which the end region of the elastic spring arm protrudes.

Advantageously, however, it may be provided that the end region of the elastic spring arm itself forms the rodlike guide element, so that a separate guide tube is dispensed with.

In a further embodiment of the invention, the connecting part is disposed displaceably along a rodlike guide element extending parallel to the threaded spindle, which is solidly joined to the bracing plate, and the connecting part is joined to the end region of the elastic spring arm associated with the force module.

Finally, in an embodiment of the invention, it is provided that the applicable force module includes a threaded spindle, disposed rotatably on the bracing plate, and the threaded spindle is in engagement with a spindle nut, to which the end region of the elastic spring arm associated with the force module is secured, and the spindle nut is disposed displaceably along a rodlike guide element that extends parallel to the threaded spindle.

Figure 2:
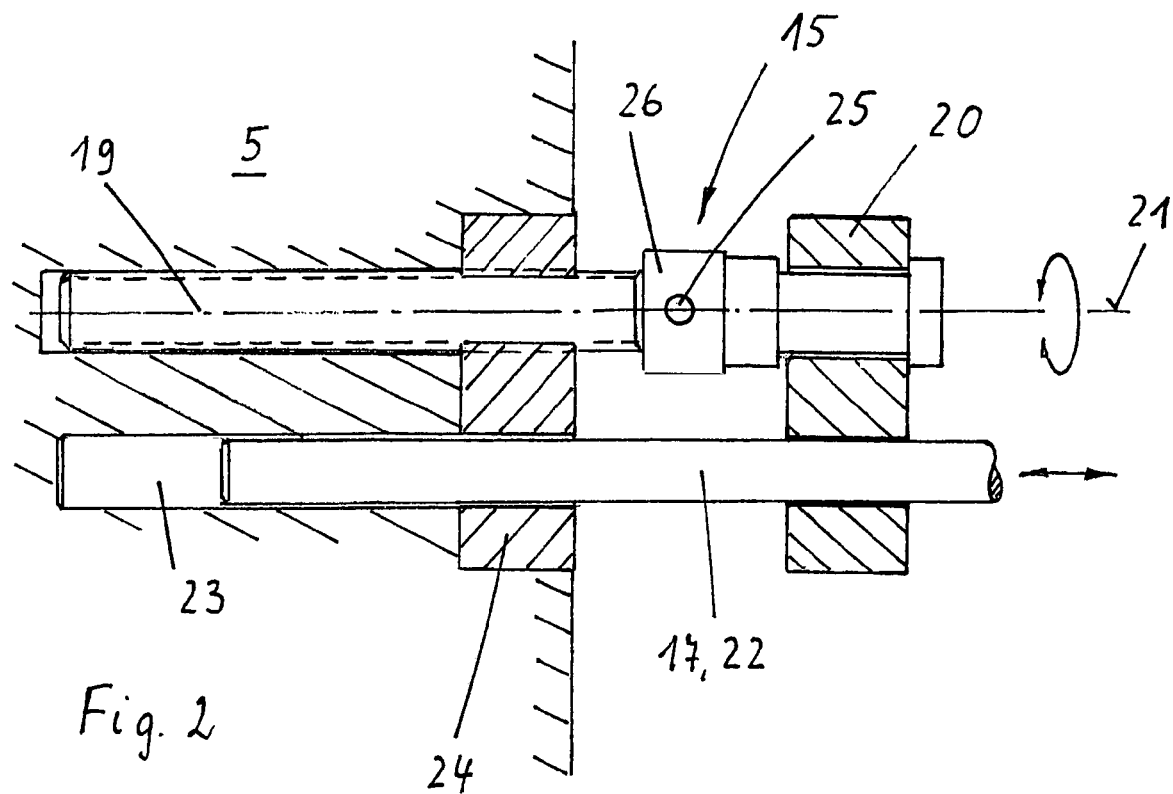
Figure 3:
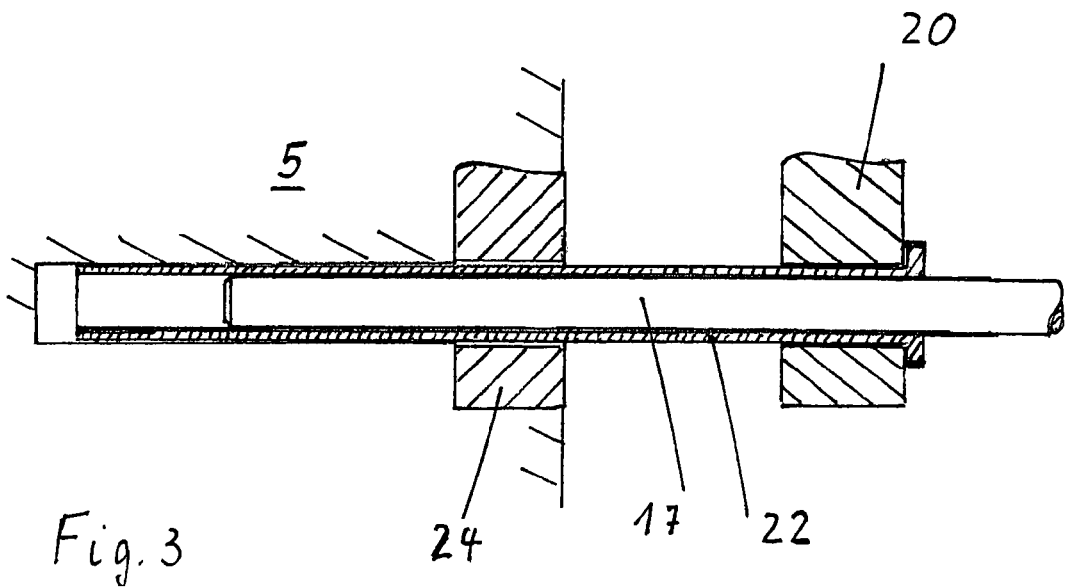

Further details and advantages of the invention will become apparent from the following exemplary embodiments, explained in conjunction with the drawings. Shown are:

FIG. 1, a top view on a device according to the invention, disposed on a dental arch of an upper jaw, with two force modules for distalizing the molars of the upper jaw;

FIG. 2, an enlarged view, shown partly in section, of one of the two force modules shown in FIG. 1, each comprising a threaded rod, connecting part, and guide element;

FIG. 3, an alternative arrangement, shown partly in section, of a guide element of the device of the invention.

In FIG. 1, reference numeral 1 indicates the schematically shown dental arch of an upper jaw.

For distalizing the molars 2 and 3, a device 4 of the invention is provided. This device has a bracing plate 5 of plastic, which rests on the palate of the upper jaw. The bracing plate 5 is secured with the aid of laterally disposed wire elements 6-9 to the bicuspids 10-13 located anteriorly of the molars 2, 3.

On the posterior end 14 of the bracing plate 5, two laterally spaced-apart force modules 15, 16, which are adjustable independently of one another, are joined to the bracing plate; the force modules are each connected via a respective elastic spring arm 17, 18 comprising a titanium-molybdenum alloy to one of the two molars 2, 3 to be distalized.

The respective force module 15, 16 includes a threaded rod 19 (FIG. 2), which can screwed into and out of the bracing plate 5; a connecting part 20, which is axially displaceable with the threaded rod 19 but is secure from rotation, and which extends perpendicular to the longitudinal axis 21 of the threaded rod 19; and a rodlike guide element 22, secured to the connecting part 20, for instance by an adhesive bond, and extending parallel to the longitudinal axis 21 of the threaded rod 19. In the exemplary embodiment shown, the guide element 22 is the end region, toward the bracing plate 5, of the elastic spring arm 17.

The guide element 22 displaceably engages a guide recess 23 of the bracing plate 5.

To obtain a secure screwed connection between the threaded rod 19 and the bracing plate 5, a metal part 24 provided with an appropriate thread is let into the bracing plate 5; this part furthermore includes a bore for precise lateral guidance of the guide element 22.

Furthermore, for manual rotation of the threaded rod 19, an actuating part 26 provided with one or more bores 25 is provided; a corresponding pin (not shown) can be introduced into the bore or bores 25 disposed perpendicular to the longitudinal axis 21 of the threaded rod 19.

As can be seen directly from FIG. 1, depending on how far the threaded rods 19 are rotated out of the bracing plate 5, a different pressure can be exerted on each of the two molars 2, 3, so that the molars 2, 3 can be individually moved backward (in FIG. 1, the restoring forces generated by the force modules 15, 16 are represented by arrows of different length).

In FIG. 3, a rodlike guide element 22 is shown, which comprises a high-grade steel tube into which the end region, comprising titanium-molybdenum alloy, of the elastic spring arm 17 is introduced. The connection between the connecting part 20, the guide element 22, and the spring arm 17 is made in this case by means of a press fit.

It is understood that the invention is not limited to the exemplary embodiments described above. For instance, the connecting part may be disposed displaceably along a rodlike guide element that extends parallel to the threaded spindle and that is joined to the bracing plate. The connecting part in this case is joined by positive engagement to the end region of the elastic spring arm associated with the force module.

The respective force module may moreover have a threaded spindle, disposed rotatably on the bracing plate, with a spindle nut associated with the threaded spindle, to which nut the end region of the elastic spring arm associated with the force module is secured. In this case, the spindle nut is disposed displaceably along a rodlike guide element which extends parallel to the threaded spindle and is joined to the bracing plate.

LIST OF REFERENCE NUMERALS

1 Dental arch
2, 3 Molars
4 Appliance
5 Bracing plate
6-9 Wire elements
10-13 Teeth, Bicuspids
14 Posterior end
15, 16 Force modules
17, 18 Elastic spring arms
19 Threaded rod
20 Connecting part
21 Longitudinal axis
22 Guide element
23 Guide recess
24 Metal part
25 Bore
26 Actuating part

What is claimed is:

1. An orthodontic appliance for distalizing opposed molars of an upper jaw of a patient, comprising:
   a) a bracing plate, which in its intended use, rests on a palate of the patient, and which can be secured, via wire elements disposed on the bracing plate, to opposed teeth that are located anteriorly of molars to be distalized;
   b) two force modules on a posterior end of the bracing plate, spaced laterally apart from one another and adjustable independently of one another, connected to the bracing plate, each force module being connectable via a respective elastic spring arm to one of the two molars to be distalized;
   c) each of the respective force modules including a threaded rod that can be screwed into and unscrewed from the bracing plate and also including a connecting part, which is axially displaceable with the threaded rod but secured from rotation and which extends perpendicular to a longitudinal axis of the threaded rod, and
   d) a rodlike guide element extending parallel to the threaded rod secured to the connecting part and on one end displaceably engaging a guide recess in the bracing plate and on another end is connected to an end region of the elastic spring arm associated with the respective force module;
   wherein the rodlike guide element is a tube; and the end region of the elastic spring arm protrudes into a tubular interior of the rodlike guide element and is constructed and arranged to move with the rodlike guide element.

2. The orthodontic appliance of claim 1, wherein the rodlike guide element comprises high-grade steel, and the elastic spring arm comprises a titanium-molybdenum alloy.

3. The orthodontic appliance of claim 1, wherein the rodlike guide element and the elastic spring arm are joined together by at least one of an adhesive and a press fit.

4. The orthodontic appliance of claim 3, wherein the rodlike guide element comprises high-grade steel, and the elastic spring arm comprises a titanium-molybdenum alloy.

* * * * *